United States Patent [19]

Ehrhardt et al.

[11] 4,138,565
[45] Feb. 6, 1979

[54] STABLE SOLUTIONS AND PROCESSES FOR THEIR PREPARATION

[75] Inventors: Lothar Ehrhardt; Ludwig Patt; Volker Hartmann, all of Nuremberg, Fed. Rep. of Germany

[73] Assignee: Sandoz Ltd., Basel, Switzerland

[21] Appl. No.: 833,784

[22] Filed: Sep. 15, 1977

Related U.S. Application Data

[63] Continuation-in-part of Ser. No. 689,969, May 26, 1976, abandoned.

[30] Foreign Application Priority Data

May 31, 1975 [DE]  Fed. Rep. of Germany ....... 2524184
Aug. 6, 1977 [DE]  Fed. Rep. of Germany ....... 2735587

[51] Int. Cl.² .......................................... C07D 519/02
[52] U.S. Cl. ..................... 544/346; 424/261; 424/250; 424/14; 215/DIG. 3; 215/365
[58] Field of Search ..................... 260/285.5, 268 PE; 424/261, 250

[56] References Cited

U.S. PATENT DOCUMENTS

| | | | |
|---|---|---|---|
| 2,073,954 | 3/1937 | Wolf | 260/285.5 |
| 2,507,831 | 5/1950 | Stoll et al. | 260/268 PE |
| 3,113,133 | 12/1963 | Hofmann et al. | 260/268 PE |
| 3,652,569 | 3/1972 | Stadler et al. | 260/268 PE |
| 3,666,762 | 5/1972 | Guttmann et al. | 260/268 PE |
| 3,755,328 | 8/1973 | Stadler et al. | 260/268 PE |
| 3,901,891 | 8/1975 | Fehr et al. | 260/268 PE |

FOREIGN PATENT DOCUMENTS

| | | | |
|---|---|---|---|
| 43402 | 11/1965 | German Democratic Rep. | 260/268 PE |
| 1175430 | 12/1969 | United Kingdom | 260/285.5 |

*Primary Examiner*—Donald G. Daus
*Assistant Examiner*—Mary Lee
*Attorney, Agent, or Firm*—Gerald D. Sharkin; Robert S. Honor; Thomas O. McGovern

[57] ABSTRACT

Solutions of certain hydrogenated ergopeptide alkaloids in mixtures of pharmacologically acceptable alcohols and water have improved stability. Preferred solvents are mixtures of ethanol, propylene glycol and glycerol containing from 15–40% wt. of water and having dielectric constants between 34 and 46. With these solutions it is not essential to carry out the filing operation under an inert atmosphere.

15 Claims, No Drawings

STABLE SOLUTIONS AND PROCESSES FOR THEIR PREPARATION

This application is a continuation-in-part of our application Ser. No. 689,969, filed on May 26, 1976, and now abandoned.

This invention relates to solutions of ergot alkaloids and their synthetic derivatives including their hydrogenated derivatives and salt forms thereof.

Solutions of such compounds in predominantly aqueous media have the disadvantage that the concentration of the active species decreases on storage, because of various decomposition reactions. For this reason it is normal practice to pass inert gas through the solution during filling of the vessels in which the solution is to be sold, and to protect the contents from air, light and high temperatures.

It is known that solutions of certain natural ergot alkaloids have improved stability when alcohols are used as solvents in place of aqueous media.

Natural ergot alkaloids, for example ergotamine, decompose in solution primarily by isomerisation at C-8 (see formula I. below) and to a lesser extent by degradation to lysergic acid and isolysergic acid derivatives. Hydrogenated ergot alkaloids, on the other hand, are not subject to decomposition by isomerisation at C-8, but decompose predominantly by degradation to corresponding aci-forms or derivatives, hydrolysis products and oxidation products. Surprisingly it has now been found that notwithstanding the difference in the mechanism of decomposition, hydrogenated ergot alkaloids have improved stability in solution when pharmacologically acceptable organic solvents, in particular alcohols, are used in place of aqueous solvents.

Such stabilized solutions of hydrogenated ergot alkaloids are also found to have greater stability than solutions of natural ergot alkaloids in the same solvents, for example alcohols.

Furthermore, it has now been found that the stability of hydrogenated ergot alkaloids in solution is a function of the dielectric constant of the solution, and that stable solutions can be obtained by the use of a solvent system comprising a mixture of water and one or more alcohols, and preferably having a dielectric constant of 50 or less. Water has a dielectric constant of 80.4, and alcohols generally in the range of approximately 25–40. Therefore, a mixture of water and one or more alcohols which has a dielectric constant of 50 or less will normally have no more than 40% by weight water content.

The present invention provides stable solutions comprising one or more hydrogenated ergopeptide alkaloids in solution in a pharmacologically acceptable alcohol or mixture thereof containing up to 40% by weight of the solution of water. By the term 'hydrogenated ergopeptide alkaloids' is included hydrogenated natural or synthetic ergopeptide alkaloids, together with their salt forms.

A preferred embodiment of the present invention is a stable solution consisting essentially of (a) a hydrogenated ergopeptide alkaloid of formula I,

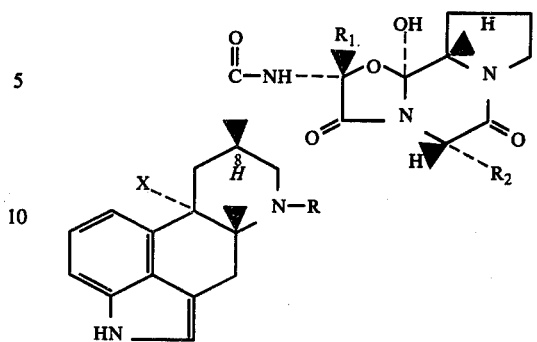

in which

R is hydrogen or alkyl having from 1 to 4 carbon atoms, other than t-butyl, $R_1$ is methyl, ethyl or isopropyl, $R_2$ is isopropyl, sec.-butyl, isobutyl or benzyl, and X is hydrogen or methoxy or a pharmaceutically acceptable acid addition salt thereof, or a mixture thereof, (b) a pharmacologically acceptable alcohol or mixture thereof and (c) up to 40% by weight of the solution of water, said solution having a dielectric constant of 50 or less.

Preferred compounds of formula I are those in which R is methyl, X is hydrogen and $R_1$ is isopropyl or methyl, provided that $R_1$ is methyl only when $R_2$ is benzyl.

Particular preferred compounds is which R is methyl and X is hydrogen are dihydro-α-ergocryptine ($R_1$ = isoproyl, $R_2$ = isobutyl), dihydro-β-ergocryptine ($R_1$ = isopropyl, $R_2$ = sec-butyl), dihydroergocornine ($R_1$ = $R_2$ = isopropyl), dihydroergocristine ($R_1$ = isopropyl, $R_2$ = benzyl) and dihydroergotamine ($R_1$ = methyl, $R_2$ = benzyl), together with their salt forms. Suitable salt forms are salts of pharmacologically acceptable acids, for example the methanesulfonate, maleate and tartrate salt forms.

Particularly preferred are dihydroergotamine (DHE) and a 1:1:1 molar mixture of dihydroergocryptine (2:1 α:β), dihydroergocornine and dihydroergocristine (dihydroergotoxin).

The dielectric constant of the solution may be measured by standard methods, for example with the help of a immersion condenser such as the model DFl 4 modified according to ASTM D 1531-595, sold by Wissenschaftlich Technische Werkstätten GmbH of Weilheim, W. Germany. Preferably, the dielectric constant of the solution lies between 30 and 46, more preferably 34 and 46.

Pharmacologically acceptable alcohols include pharmacologically acceptable monofunctional alcohols having up to 18 carbon atoms, preferably up to 10 carbon atoms and most preferably up to 3 carbon atoms. An especially preferred alcohol of this type is ethanol. Further alcohols which may be used according to the invention include pharmacologically acceptable polyfunctional alcohols having up to 6, preferably 2 or 3 hydroxy groups, and up to 6, preferably 2 or 3 carbon atoms, especially glycerol and propylene glycol. Polyfunctional alcohols may also be used in polymeric form, for example polyalkylene glycols, especially polyethylene glycol, polypropylene glycol or their copolymers, having a molecular weight from 200 to 20,000, preferably from 200 to 600. A particularly suitable polyalcohol is a polyethylene glycol with a molecular weight of approximately 400.

The above mono- and polyfunctional alcohols may be used according to the invention either alone or, advantageously, in the form of mixtures. If one of the mono- or polyfunctional alcohols should be a solid at room temperature, an alcohol which is liquid at room temperature may suitably be used as a co-solvent.

When a mixture of monofunctional and polyfunctional alcohols is used, the monofunctional and the polyfunctional alcohols should be present in a ratio of from 1:0.1 to 1:100 by weight, preferably in a ratio of from 1:1 to 1:10, more preferably of from 1:1 to 1:4 by weight. A particularly preferred range of ratios is from 1:1 to 1:2, preferably 1:2 by weight. Mixtures of ethanol and propylene glycol or ethanol, propylene glycol and glycerol, are particularly preferred.

The solutions according to the invention may further contain, as additional solvents, pharmacologically acceptable organic esters and ethers, particularly those formed from the above-mentioned mono- and polyfunctional alcohols and fatty acids having from 12–18 carbon atoms, from example stearic acid, palmitic acid and oleic acid; or fatty alcohols having from 12 to 18 carbon atoms, for example lauryl alcohol, cetyl alcohol and stearyl alcohol.

The water content of the solution must not be greater than 40% by weight, and preferably lies between 15 and 40% by weight.

Although the concentration of the compound of formula I in the solutions is not critical, it is preferred to use solutions with a concentration of active species of from 0.01 to 1% wt/volume, preferably from 0.1 to 0.5% wt/volume. It is to be understood that the concentration to be used will depend upon the application for which the solution is intended.

The solutions may in addition contain further solubilising additives from example acids, particularly methanesulfonic acid, maleic acid, tartaric acid, etc.

The preparation of the compositions according to the invention is carried out by dissolving the compound of formula I in the solvent or solvent mixture by stirring at room temperature (15–25° C). This may be done under an atmosphere of inert gas and with exclusion of daylight, but these precautions are not essential in view of the improved stability of the solutions according to the invention. The solution may be filtered under pressure, preferably under inert gas pressure, and used to fill suitable vessels. It is not essential to carry out the filling operation under an inert gas atmosphere.

The preparation of solvent mixtures is carried out in conventional manner, and where one of the solvent components is solid at room temperature, mixing is suitably carried out at higher temperatures, e.g. at up to 80° C. Ethanol may advantageously be used as co-solvent.

Compositions according to the invention are useful as pharmaceuticals in the same way as corresponding aqueous solutions of the same active species. They may be administered orally, and may for this purpose be made up in vessels designed to dispense unit dosages, for example dropped bottles; or parenterally, in which case the solutions will normally be sterilized and may be sealed in ampoules of unit dosage. The compositions may also be administered in the form of nasal drops or nasal spray.

For oral administration, a preferred solvent mixture is an ethanol/propylene glycol or ethanol/propylene glycol/glycerol mixture as described above, containing up to 40%, preferably from 15 to 40%, by weight of water. Compositions containing at least 15% by weight of water have a more palatable taste for oral administration. For parenteral administration, it is undesirable to use solvent mixtures containing more than 5% of ethanol, and a preferred solvent is propylene glycol containing up to 40%, preferably from 15 to 40%, by weight of water. The presence of at least 15% by weight of water lowers the viscosity of the solvent and thereby allows easier and less painful injection of the composition.

As is well known, dihydroergotoxin may, for example, be used in the treatment of conditions arising from cerebral vascular insufficiency and arteriosclerosis. A recommended oral dosage is 1.5 ml of a 0.1% wt./vol. solution, three times daily. As is also well known, dihydroergotamine is indicated, for example, in the treatment of orthostatic hypotension and the prophylaxis of migraine, suitable oral dosages being 0.5–1.5 ml of a 0.2% wt./vol. solution, 2 to 3 times daily. Dihydroergotamine may also be administered parenterally for the relief of acute migraine attacks, a suitable dose being one ampoule containing 1 ml of a 0.1% wt./vol. solution, administered 1–3 times as required at 30 minute intervals. The following Examples illustrate the invention.

EXAMPLE 1

A mixture of 50.0 g propylene glycol and 41.9 g 94% ethanol was prepared and in this mixture was dissolved, by stirring at room temperature under a nitrogen atmosphere, 0.1 g of a mixture of dihydroergocristine, dihydroergocryptine and dihydroergocornine (1:1:1). After filtration under pressure, the solution was used to fill dropper bottles.

EXAMPLE 2

A mixture of 40.0 g propylene glycol, 34.0 g 94% ethanol and 25.0 g anhydrous glycerol was prepared and in this mixture was dissolved, by stirring at room temperature under a nitrogen atmosphere, 0.1 g of a mixture of dihydroergocristine, dihydroergocryptine and dihydroergocornine (1:1:1). After filtration under pressure, the solution was used to fill dropper bottles.

EXAMPLE 3

A mixture of 65.3 g propylene glycol and 34.7 g 94% ethanol was prepared and in this mixture was dissolved, by stirring at room temperature under a nitrogen atmosphere, 0.1 g of a mixture of dihydroergocristine, dihydroergocryptine and dihydroergocornine (1:1:1). After filtration under pressure, the solution was used to fill dropper bottles.

EXAMPLE 4

In sterile propylene glycol (100 g) was dissolved, by stirring at room temperature under a nitrogen atmosphere, 0.05 g of a mixture of dihydroergocristine, dihydroergocryptine and dihydroergocornine (1:1:1). After filtration under pressure, the solution was sealed into sterile ampoules.

EXAMPLES 5–7

Solutions were made up as described in Example 1–3, but containing, as active species, 0.1 g of dihydroergotamine methanesulfonate.

EXAMPLE 8

A solution was made as described in Example 4, but containing, as active species, 0.05 g of dihydroergotamine methanesulfonate.

EXAMPLE 9-16

(A) Preparation of Solvent Mixtures

Solvent mixtures 1-4 were prepared by mixing together the quantities of solvents shown in the following table. The table also gives the water content in % by weight (taking into account the 6% water content of the 94% ethanol), and the measured dielectric constant. In all four mixtures, ethanol, glycerol and propylene glycol were present in 33:26:41 ratio by weight.

| Mixture No. | 1 | 2 | 3 | 4 |
|---|---|---|---|---|
| Weights (g) | | | | |
| ethanol (94%) | 1183 | 1051 | 1992 | 1728 |
| glycerol | 869 | 773 | 1464 | 1272 |
| propylene glycol | 1391 | 1236 | 2344 | 2040 |
| distilled water | 303 | 686 | 2256 | 3056 |
| Water content by wt. | 10.0% | 20.0% | 29.5% | 39.0% |
| Dielectric constant | 34.2 | 37.7 | 41.6 | 45.8 |

(B) Preparation of Solutions

EXAMPLE 9

In 1 liter of solvent mixture 1 was dissolved 1.0 g of dihydroergotoxin methanesulfonate, by stirring at room temperature under a nitrogen atmosphere. After filtration under nitrogen pressure, the solution was used to fill dropper bottles.

EXAMPLE 10

In 1 liter of solvent mixture 1, prepared under sterile conditions, was dissolved 2.0 g of dihydroergotamine methanesulfonate, by stirring at room temperature. After filtration under nitrogen pressure, the solution was used to fill dropper bottles.

EXAMPLES 11-16

Following the procedure of Examples 9 and 10, solutions were prepared using solvent mixtures 2-4 in place of solvent mixture 1.

EXAMPLE 17

In 100 ml of a mixture of 80 parts by wt. sterile propylene glycol and 20 parts by wt. water for injection was dissolved, by stirring at room temperature, 0.1 g of dihydroergotamine methanesulfonate. After filtration under nitrogen pressure, the solution was sealed into sterile ampoules, each containing 1 ml of solution

EXAMPLE 18

10.0 g of polyethylene glycol of molecular weight 400 was dissolved in a mixture of 40.0 g 94% ethanol and 23.0 g propylene glycol. 20.0 g water was added, to give 100 ml of solvent mixture in which was dssolved 0.1 g dihydroergotoxin methanesulfonate by stirring at room temperature. After filtration under nitrogen pressure, the solution was used to fill dropper bottles.

EXAMPLE 19

6.0 g of a mixture of cetyl and stearyl alcohol was dissolved in 68.6 g 94% ethanol. 8.5 g water was added, to give 100 ml of solvent mixture in which was dissolved 0.1 g dihydroergotoxin methanesulfonate by stirring at room temperature. After filtration under nitrogen pressure, the solution was used to fill dropper bottles.

What is claimed is:

1. A hydrogenated ergopeptide alkaloid solution which is stable against decomposition on storage consisting essentially of
   (a) a hydrogenated ergopeptide alkaloid or a pharmacologically acceptable acid addition salt thereof, or a mixture thereof
   (b) a pharmacologically acceptable alcohol or mixture thereof, and
   (c) up to 40% by weight of the solution of water, and having a dielectric constant of 50 or less.

2. A stable solution according to claim 1 consisting essentially of
   (a) a hydrogenated ergopeptide alkaloid of formula I,

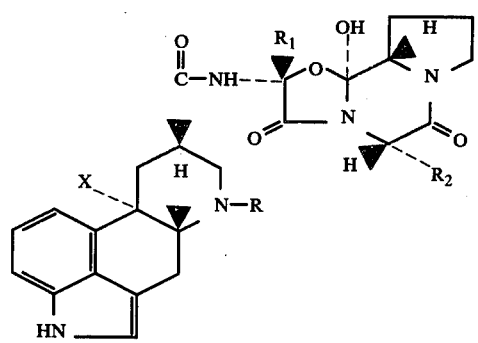

in which
   R is hydrogen or alkyl having from 1 to 4 carbon atoms, other than t-butyl,
   $R_1$ is methyl, ethyl or isopropyl,
   $R_2$ is isopropyl, sec.-butyl, isobutyl or benzyl, and
   X is hydrogen or methoxy or a pharmaceutically acceptable acid addition salt thereof, or a mixture thereof,
   (b) a pharmacologically acceptable alcohol or mixture thereof and
   (c) up to 40% by weight of the solution of water, said solution having a dielectric constant of 50 or less.

3. A solution according to claim 2 having a dielectric constant between 30 and 46.

4. A solution according to claim 3 having a dielectric constant between 34 and 46.

5. A solution according to claim 2 in which component (a) is a compound of formula I, stated in claim 2, in which
   R is methyl
   X is hydrogen and
   $R_1$ is isopropyl or methyl,
provided that $R_1$ is methyl only when $R_2$ is benzyl.

6. A solution according to claim 2 in which component (b) is propylene glycol.

7. A solution according to claim 2 in which the proportion of component (c) is from 15 to 40% by weight.

8. A solution according to claim 2 in which component (b) is a mixture of
   ($b_1$) a pharmacologically acceptable monofunctional alcohol having up to 18 carbon atoms, or mixtures thereof, and
   ($b_2$) a polyfunctional alcohol having up to 6 carbon atoms and 6 hydroxy groups or a polymeric polyfunctional alcohol having a molecular weight of from 200 to 20,000, or mixtures thereof, the weight ratio of component ($b_1$) to component ($b_2$) being 1:0.1 to 1:100.

9. A solution according to claim 8 in which the concentration of component (a) is from 0.01 to 1% by weight, component ($b_1$) has up to 10 carbon atoms, the ratio of component ($b_1$) to component ($b_2$) is 1:1 to 1:10, and the proportion of component (c) is from 15 to 40% by weight.

10. A solution according to claim 9 in which component ($b_1$) has up to 3 carbon atoms and component ($b_2$) is a polyfunctional alcohol of 2 or 3 carbon atoms and 2 or 3 hydroxy groups or a polymeric polyfunctional alcohol having a molecular weight of 200 to 600.

11. A solution according to claim 10 in which the ratio of component ($b_1$) to component ($b_2$) is 1:1 to 1:2.

12. A solution according to claim 10 in which component ($b_1$) is ethanol and component ($b_2$) is propylene glycol or glycerol or mixtures thereof.

13. A solution according to claim 10 in which component (a) is dihydroergotamine.

14. A solution according to claim 10 in which component (a) is dihydroergotoxin.

15. A method of preparing a hydrogenated ergopeptide alkaloid solution which is stable to decomposition on storage according to claim 2, consisting essentially of dissolving a compound of formula I, stated in claim 2, or a pharmaceutically acceptable acid addition salt thereof or a mixture thereof in a solvent consisting essentially of:

(a) a pharmacologically acceptable alcohol or a mixture thereof (b) up to 40% by weight of the solution of water, said solvent having a dielectric constant of 50 or less, at a temperature of 15 to 25° C.

* * * * *